United States Patent [19]
Kertzner

[11] Patent Number: 5,649,930
[45] Date of Patent: Jul. 22, 1997

[54] ORTHOPEDIC CENTERING TOOL

[76] Inventor: Richard I. Kertzner, 3021 Mountain Park Dr., Calabasass, Calif. 91302

[21] Appl. No.: 592,555

[22] Filed: Jan. 26, 1996

[51] Int. Cl.⁶ .................................................. A61B 17/17
[52] U.S. Cl. ................................................. 606/96; 606/80
[58] Field of Search ............................. 606/59, 62, 63, 606/64, 80, 86, 87, 95, 96, 97, 98, 104

[56] References Cited

U.S. PATENT DOCUMENTS

| 4,257,411 | 3/1981 | Cho | 606/96 |
| 4,541,424 | 9/1985 | Grosse et al. | 606/98 |
| 4,672,957 | 6/1987 | Hourahane | 606/80 |

FOREIGN PATENT DOCUMENTS 634460  3/1950  United Kingdom .

*Primary Examiner*—Michael Buiz
*Assistant Examiner*—David O. Reip
*Attorney, Agent, or Firm*—Elliott N. Kramsky

[57] ABSTRACT

A tool for guiding a surgical drill bit through the center of a target obstruction within a bone. An adjustable frame includes a pair of right angle sections mounted in a mirror image relationship. The sections are adjustably clamped to one another and, in turn, secure a vertical sleeve for guiding a surgical drill bit and a horizontal sleeve for accommodating an anchor pin within a coplanar arrangement. Various clamps associated with the frame elements and the sleeves permit a surgeon to adjust the tool so that the drill bit is guided through the vertical sleeve to the approximate center of the bone immediately below the obstruction while the pin anchors the frame to the bone.

7 Claims, 3 Drawing Sheets

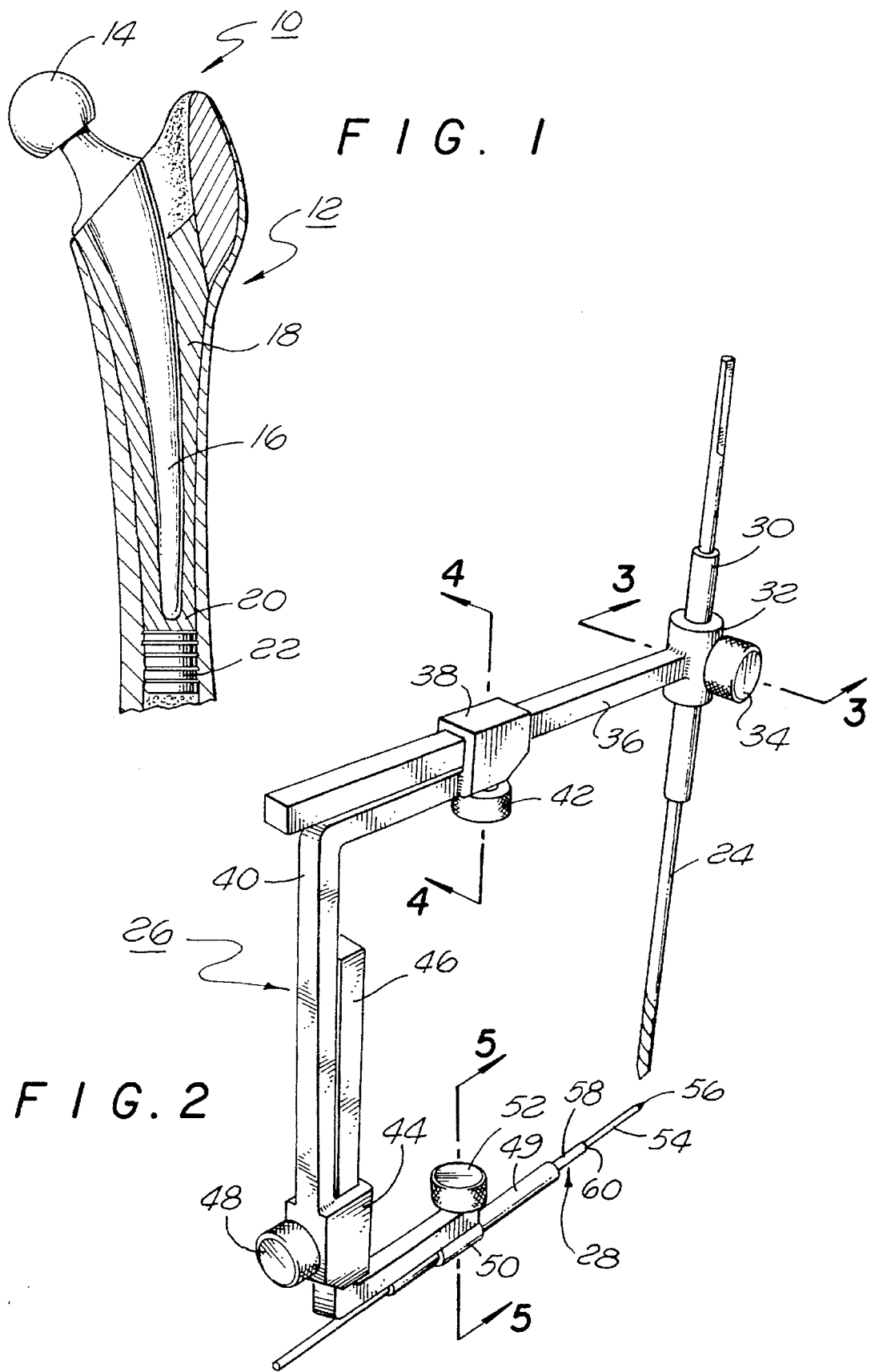

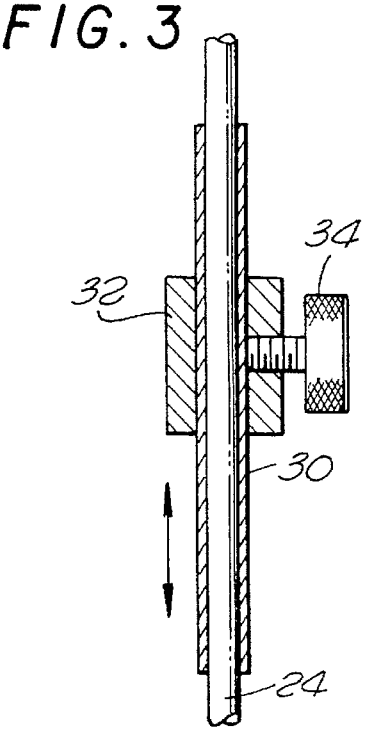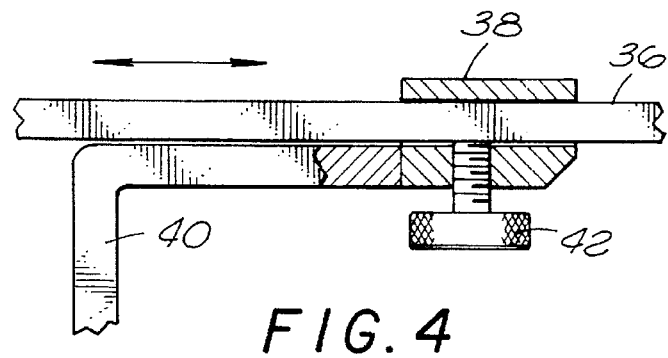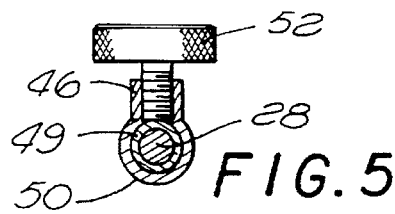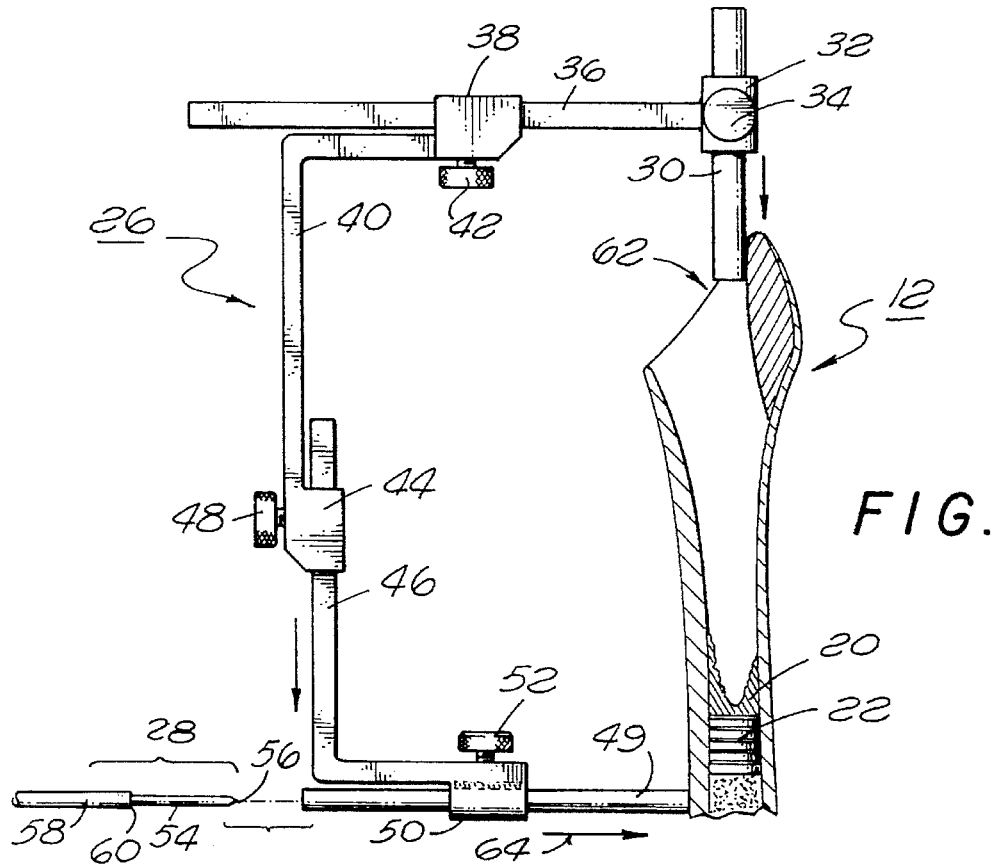

ORTHOPEDIC CENTERING TOOL

BACKGROUND

1. Field of the Invention

The present invention relates to devices for facilitating orthopedic procedures. More particularly, this invention pertains to a tool for use in centering the travel of an elongated surgical tool, such as a drill bit, to thereby avoid perforation of bone tissue.

2. Description of the Prior Art

A number of important orthopedic surgical procedures require the use of a potentially-harmful elongated cutting tool, such as a drill bit, at a distance removed from the surgeon's ready control. Such procedures include the revision of hip protheses, and fixation of acute fractures and non-unions that routinely require the clearing of a channel within a long bone. For example, FIG. 1 is a side elevation view, partly in section, of a hip replacement including a prosthesis 10 fixed within a human femur 12. The prosthesis is fabricated, for example, of stainless steel and includes a metal ball or prosthetic femoral head 14 coupled to a prosthetic hip socket (not shown). The lower portion of the prosthesis 10 extends to and terminates in an elongated stem 16. The stem 16 extends into the femoral canal where it is anchored to the bone by means of an appropriate cement 18 (a mixture of a monomer and a polymer).

The hardened cement 18 surrounds the stem 16 extending beneath it to form a solid region within the surrounding wall of bone tissue known as a cement "plug" 20. Optionally, a stop or restrictor 22 of plastic composition is fitted within the femur 12 for increasing the backpressure on the cement 18 as it hardens and improving the quality of the cement-to-bone tissue bond.

Hip surgeries of the type illustrated in FIG. 1 presently experience useful lives of from 10 and 20 years. Gradual breakdown or loosening of the bond between the cement and bone tissue occurs over time, causing the patient to experience pain. When such pain becomes significant, a redoing of the former replacement is indicated in which the existing prosthesis is removed and a new prosthesis attached in its place. The required surgical procedure involves removal of the hardened cement and optional restrictor in addition to the former prosthesis, prior to insertion of the new device. The second hip replacement procedure often employs a non-cement fixation technique due to the thinning and reduced adhesion of existing bone tissue. The latter prosthesis may, for example, be formed with beads or mesh, providing a surface that encourages interdigitation of bone tissue thereon. An alternative technique is to use cement again injected into and pressurized within a femoral canal cleared of all debris.

The hip prosthesis substitution is begun by removal of all foreign objects from the femoral canal. The actual prosthesis may be readily removed during surgery, leaving the mantle of hardened cement and possibly a plastic restrictor. Removal of the structures associated with the former prosthesis becomes more complicated and risky as one progresses further and further from the top or head of the bone into the femoral canal. The uppermost cement is not terribly difficult for the surgeon to remove due to good visibility and accessibility. In addition, the removal procedure is facilitated in this region by the existence of a large central channel or void left after removal of the stem of the prosthesis. Such evacuated area extends the region of access and visibility, and thus the work region, well into the femoral canal. A number of techniques are useful in this area, including the use of power burrs, hand-held chisels and ultrasound (to "melt" the cement). All are reasonably satisfactory for removing the cement mantel from surrounding bone tissue. As one proceeds further to the region of the cement plug, discussed above, visibility and accessibility limitations begin to crop up. Maintenance of adequate lighting is difficult and further obscuration is caused by the increased presence of blood.

The nature of the surgeon's work is complicated by the fact that the plug region of the cement mantle and the optional restrictor lie beneath the access channel or void left by removal of the prosthesis. A number of techniques are commonly employed to remove the cement plug and restrictor. Some involve the use of elongated drill bits, burrs, or hand-held chisels to break through, fragment or create a hole in the cement plug. An elongated tool having a hooked end can then be inserted through the obstruction and an upwardly directed force applied to lift and remove these remaining obstructions. Alternatively, if a drill hole has been made, a device may be threaded into the hole with a similarly directed force applied.

Visibility and alignment difficulties in the plug region create a very dangerous environment in which to operate a drill bit, burr or chisel. Misalignment of these elongated instruments may result in the perforation of bone tissue. The surgeon, however, must remove (or displace distally beyond the tip of the new prosthesis) all cement from the prior prosthesis (along with the plastic stop) despite the potential dangers. Leaving cement can adversely affect preparation of the femur. Other instrumentation as well as the prosthesis may be misdirected by any remaining cement mantle. In addition, the remaining surface may be incapable of providing good adhesion.

In order to overcome the serious perforation risk, x-ray or like equipment is often employed to assure centering of the potentially-harmful tool with respect to the surrounding bone tissue. Such equipment is bulky and therefore creates difficulties for the surgeon who must work within a limited area. Additionally, this equipment can act as a source of contamination. Another method involves excising a viewing "window" in the bone. This, of course, complicates the operation, increasing its duration, the loss of blood and the risk of eventual bone fracture.

SUMMARY OF THE INVENTION

The present invention addresses the aforesaid problems of the prior art by providing, in a first aspect, apparatus for guiding an elongated surgical tool through the interior of a bone. Such apparatus includes a first elongated sleeve for slidably guiding the tool. Means are provided for maintaining the axis of the first sleeve in a vertical orientation and for selectively fixing the height of the first sleeve.

An elongated anchor pin is provided. A second elongated sleeve is provided for slidably guiding the anchor pin. Means are provided for holding the second sleeve perpendicular to and coplanar with the axis of the first sleeve and for selectively fixing the horizontal disposition of the second sleeve.

In another aspect, the invention provides apparatus for internally positioning an elongated surgical tool with respect to a bone. Such apparatus includes an adjustable frame. The frame includes a first means for adjustably vertically positioning a first sleeve and a second means for adjustably horizontally positioning a second sleeve. The first sleeve is arranged to slidably receive the drill bit while the second sleeve is arranged to receive an anchor pin in slidable relationship. A first means is provided for fixing the position of the first sleeve with respect to the bone and a second means is provided for fixing the position of the second sleeve with respect to the bone.

The preceding features of the invention will be further appreciated from the detailed description that follows. Such description is accompanied by a set of drawing figures. Numerals of the drawing figures, corresponding to those of the written description, point to the various features of the invention. Like numerals refer to like features throughout both the drawing figures and the written text.

BRIEF DESCRIPTION OF THE DRAWINGS

FIG. 1 is a side elevation view, partly in section, illustrating a hip prosthesis fixed to a femur;

FIG. 2 is a perspective view of the orthopedic positioning tool of the invention with surgical drill in place;

FIG. 3 is a sectional view for illustrating the drill clamp of the positioning tool taken at line 3—3 of FIG. 2;

FIG. 4 is a sectional view of the horizontal extension adjustment clamp taken at 4—4 of FIG. 2;

FIG. 5 is a sectional view of the positioning tool taken at line 5—5 of FIG. 2 and illustrating the anchor pin sleeve clamp in detail;

FIG. 6 is a side elevation view, partially in section, illustrating the initial setup or configuration as engaged to the patient for axially positioning a surgical drill bit;

DETAILED DESCRIPTION OF THE PREFERRED EMBODIMENT

Figure 7:
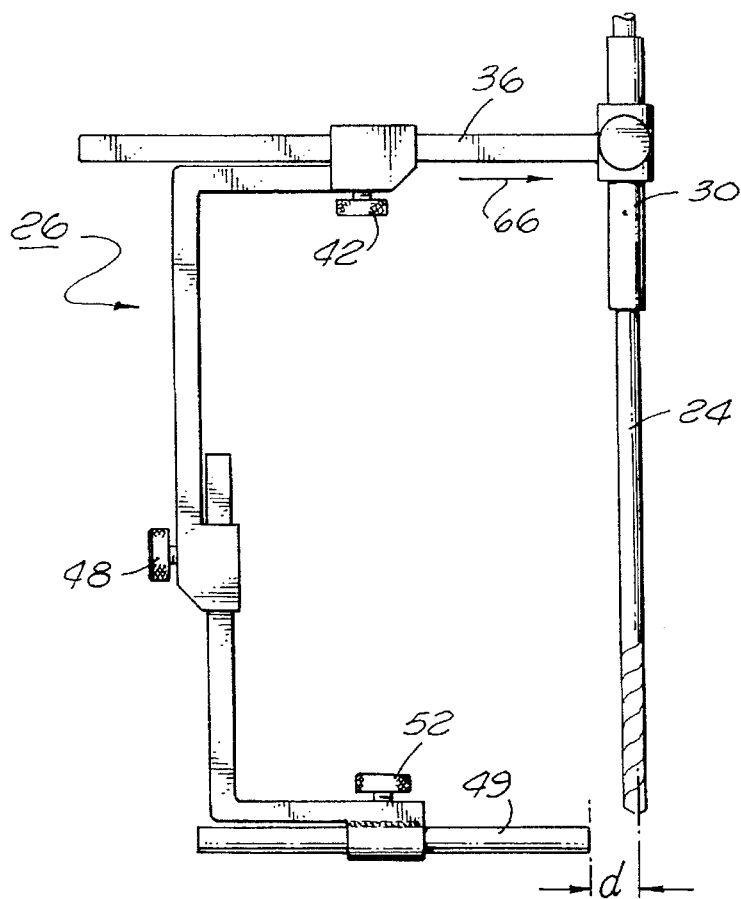
FIG. 7 is a side elevation view of the invention generally in accordance with the prior figure as arranged and disengaged from the patient for use subsequent to the step of femur x-ray.

FIG. 2 is a perspective view of the orthopedic positioning tool of the invention with surgical drill bit 24 in place. As will be seen below, the tool of the invention is employed to assist and guide an operating surgeon in directing the drill bit 24 through the interior of a bone as, for example, the femur 12 illustrated in FIG. 1, supra. As explained above, a carefully guided and positioned drill bit 24 is sometimes required in the performance of surgery to replace a failed hip prosthesis. The drill bit 24 must make an access hole through a plug of hardened cement mantle (and, perhaps, an underlying plastic restrictor) to permit subsequent entry of an elongated threaded device or a hooked tool such as that available from DePuy Corporation of Warsaw, Ind. under commercial designation 6020-13.

While the tool of the invention provides the surgeon with advantages as described in detail when performing hip replacement surgery, its utility is not limited to this procedure. Rather, the tool may be employed in conjunction with other orthopedic procedures that require the creation of an aperture through an obstruction within a bone in an internal region where a significant risk of perforation of bone tissue exists. Such other procedures are associated with the insertion of a rod into a long bone to correct fracture non-union. Such non-union often generates dense hard bone on either side of the fracture requiring a hole therethrough for receiving the rod that serves as an internal splint.

Returning to FIG. 2, the orthopedic positioning tool of the invention generally comprises an adjustable frame 26 for positioning the vertical drill bit 24 with respect to a horizontal anchor pin 28, the bit 24 and the anchor pin 28 constituting the only illustrated elements that penetrate the bone. As will be disclosed below, the anchor pin 28, upon adjustment, stabilizes the frame 26 and the path of travel of the drill bit 24 while locating the center of the femoral channel at the targeted bone depth (i.e. at the bottom of the internal obstruction). In this way, the anchor pin 28 cooperates with the drill bit 24 through adjustment made to the frame 26 to position and guide the bit safely through the femoral canal and without undue risk of bone perforation.

The drill bit 24 is located in guided slidable relationship by means of a vertical sleeve 30. The vertical sleeve 30 is elongated and adjustably fixed within a vertical cylindrical clamp 32. FIG. 3 is a sectional view that illustrates the vertical cylindrical clamp 32 for fixing the position (height) of the vertical sleeve 30. The vertical sleeve 30 is both upwardly and downwardly adjustable with the desired position made fixable by means of a setting screw 34. The significance of the vertical sleeve 30 height adjustment to operation of this invention will become further apparent from the discussion of operation that follows.

The vertical cylindrical clamp 32 fixed to an end of a horizontal upper bar 36. Just as the height of the vertical sleeve 30 is adjustable by means of the clamp 32, the horizontal displacement of the sleeve 30 and, hence, of the drill bit 24, is similarly adjustable via extension and vice versa of the upper bar 36. Once a suitable adjustment has been made, it may be fixed by means of an upper end clamp 38 that is fixed to one end of an upper right angle section 40 of the adjustable frame 26.

It is an important feature of the invention that the frame 26, though adjustable, maintains the orientations of the vertical drill bit 24 and the horizontal anchor pin 28 within a shared plane. This is accomplished by maintaining the elements of the frame within the same plane. FIG. 4 is a sectional view of the horizontal adjustment clamp 38 taken at 4—4 of FIG. 2. As can be seen, a tightening screw 42 is provided for fixing the desired horizontal displacement of the vertical cylindrical clamp 32 located at the end of the horizontal upper bar 36. Referring to FIGS. 2 and 4 in combination, it can be seen that the coplanar arrangement of the frame 26 is achieved by an arrangement of members of generally-square cross section. When held by clamps, including the clamp 38 and a clamp 44 fixed to the opposed end of the upper right angle section 40 (which engages a lower right angle section 46) in a fixably-adjustable mirror image relationship, a generally c-shaped frame geometry is defined. This provides both vertical and horizontal adjustability of the spatial locations of the vertical drill bit 24 and the horizontal anchor pin 28. The desired height of the c-shaped frame is fixed by means of a setting screw 48.

FIG. 5 is a cross-sectional view of the invention taken at line 5—5 of FIG. 2 for illustrating the arrangement for fixably securing the desired extension of a horizontally-oriented anchor pin sleeve 49. Referring to that figure in combination with FIG. 2, the sleeve 49 is held within a horizontal cylindrical clamp 50 that is fixed to the bottom of the horizontal section of the lower right angle section 46. Once the extension of the anchor pin sleeve 49 is satisfactory (as ascertained by the surgeon infra), it is fixed by means of a set screw 52. Thus, the frame 26 provides full horizontal and vertical adjustability for the vertical sleeve 30 and the horizontal cylindrical sleeve 50 (and associated anchor pin 28) within a single plane. In addition, the various clamps and set screws offer the requisite fixability of frame configuration required for operation during drilling.

Referring back to FIG. 2 with particular attention to the anchor pin 28 which is slidably located within the horizontal cylindrical sleeve 49, it may be noticed that the pin 28 comprises a frontal section 54 of reduced diameter that terminates in a pointed tip 56. The remainder of the anchor pin 28 comprises a rear section 58 of greater diameter, forming a shoulder 60 therebetween. The shoulder 60 will be seen to act as a "stop" when the pin 28 is inserted into bone tissue. The anchor pin 28 is selected according to the length of its reduced-diameter section 54, giving the surgeon a choice of pins according to bone diameter, discussed below.

Figure 8:
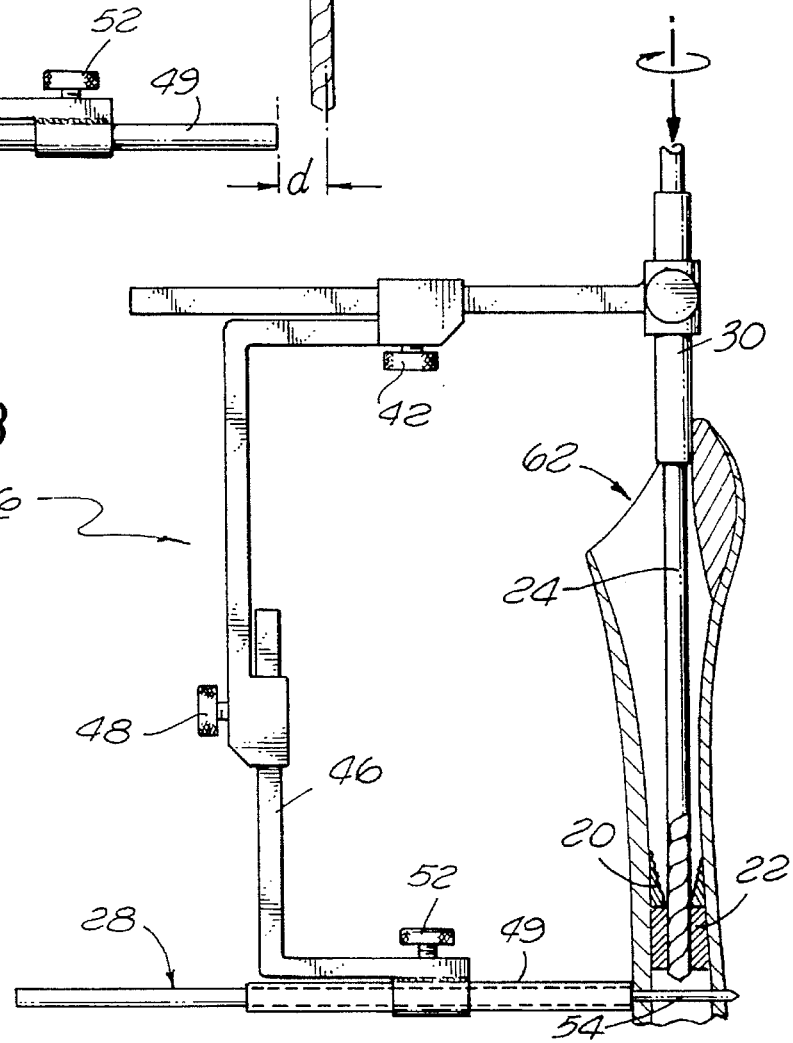
FIG. 8 is a side elevation view of the invention in use with surgical drill for creating a centered aperture in a plug and restrictor.

FIGS. 6 through 8 are a series of views for illustrating the process of frame adjustment in relation to a surgical procedure, such as hip replacement, requiring the cutting of a hole through an obstruction within a hollow bone structure. Referring first to FIG. 6, a side elevation view is presented of the initial setup or configuration for axially positioning a surgical drill bit. It will be appreciated that, while reference shall be made to the complete anatomical and operating environment during the discussion that follows, only bone tissue is illustrated for purposes of clarity.

The process of adjusting the frame 26, which, of course, takes place during surgery, is begun by inserting the vertical sleeve 30 (without a bit) into an entry hole 62. The position of the entry hole 62 is, in the redoing of a hip replacement, determined by the cavity or void left after removal of the stem of the existing prosthesis. In the event of a procedure in which an entry hole must be created, the surgeon's "feel" is relied upon to determine a proper location, generally at the head of the bone.

The height of the generally c-shaped frame 26 is adjusted with the vertical sleeve 30 at the entry hole 62 as shown (a position fixed by means of the set screw 34) by appropriate extension of the lower right angle section 46. Once the correct dimension is obtained as shown it is fixed by tightening the set screw 48. The position of the cement plug 20 within the femur 12 (and the optional underlying restrictor 22) is known from x-rays taken prior to the operation. Thus, the adjustment at the clamp 44 subsequent to fixing of the position of the vertical sleeve 30 is relatively straightforward.

Once the clamps 32 and 44 have been fixed, the horizontal anchor pin sleeve 49 is inserted into the horizontal cylindrical sleeve 50 through an approximately ½ inch incision in the surrounding tissue. The incision is spread and the sleeve 49 advanced in the direction 64 (approximately collinear with a radius of the cross-section of the femur 12) until the configuration of FIG. 6 is attained, the end of the horizontal cylindrical sleeve 49 touching the femur 12 as shown.

Once the configuration of FIG. 6 has been set, the centering tool of the invention is removed from the patient and the drill bit 24 inserted into the vertical sleeve 30 as shown in FIG. 7. An x-ray is made of the region beneath the obstruction to determine the diameter of the bone in this area. (Of course, this determination is made from x-rays taken prior to surgery.) With the diameter known, the vertical sleeve 30 is then displaced horizontally from the end of the anchor pin sleeve 49 by an amount "d". This is accomplished by loosening the set screw 42 and sliding the horizontal upper bar 36 in the direction 66. The distance d is equal to one-half the diameter of the femur 12 in the region immediately beneath the obstruction (that is, at the depth that the end of the anchor pin sleeve 49 contacts the femur 12 as shown in FIG. 6). The vertical distance, as mentioned earlier, is determined by preoperative x-ray. Once the vertical sleeve 30 has been displaced by an appropriate amount, the set screw 42 is tightened, fixing the configuration of FIG. 7.

The invention is again engaged to the patient through the existing incisions with the positions of the vertical cylindrical sleeve 30 and the horizontal anchor pin sleeve 49 fixed as shown. The vertical cylindrical sleeve 30 is reinserted into the entrance hole 62 at the head of the femur 12. Having determined the diameter of the femur 12 in the relevant region, the surgeon then selects an appropriately-sized anchor pin 28 for insertion into the guiding horizontal sleeve 49. The appropriate sized anchor pin 28 is determined by the relationship between the length of the reduced diameter frontal section 54 and bone diameter. Bone diameter at the relevant depth can be determined by x-ray before the procedure is begun. A correctly-sized anchor pin 28 should slide through the sleeve 49 to extend through the femur 12 as shown. The shoulder 60 acts as a stop to penetration at the wall of the femur 12. The surgeon can, through feel, establish the proper point to insert the pin so that it passes through the approximate center of the bone's cross-section. The shoulder 60 prevents the anchor pin 28 from continuing unnecessarily deep into soft tissue beyond the opposed wall of the femur 12.

After the configuration of FIG. 8 is fixed, the drill bit 24 is again inserted into the vertical sleeve 30 and actuated, either manually or under external power, to cut downwardly within the femoral canal as required by the surgical procedure. The surgeon may concentrate upon the operation, assured that the potentially-dangerous elongated cutting tool is properly aligned.

Thus it is seen that the present invention provides apparatus for centering and guiding the travel of an elongated surgical cutting device, such as a drill bit, through a bone. While the application of this apparatus to hip replacement surgery has been extensively discussed, it should be kept in mind that the invention is suitable for numerous other applications and procedures that require the use of an elongated cutting tool working at distances that limit the surgeon's ready control and visibility. Such applications, include, but are not limited to, insertion of rods in long bones for setting incomplete fractures.

While the present invention has been described with reference to its presently preferred embodiment, it is not limited thereto. Rather, this invention is limited only insofar as it is defined by the following set of patent claims and includes within its scope all equivalents thereof.

What is claimed is:

1. Apparatus for guiding an elongated surgical tool through the interior of a bone comprising, in combination:
    a) a first elongated sleeve for slidably guiding said tool;
    b) means for maintaining the axis of said first sleeve in a vertical orientation;
    c) means for selectively fixing the height of said first sleeve;
    d) an elongated anchor pin;
    e) a second elongated sleeve for slidably guiding said pin;
    f) a frame including an upper bar, an upper right angle section and a lower right angle section oriented within a common plane;
    g) first means for adjustably fixing the position of said upper bar with respect to said upper right angle section and second means for adjustably fixing the position of said upper right angle section with respect to said lower right angle section; and
    h) means for selectively fixing the horizontal disposition of said second sleeve.

2. Apparatus as defined in claim 1 wherein:

a) each of said upper bar, said upper right angle section and said lower right angle section is of substantially square cross section; and b) said first means comprises a clamp fixed to the upper end of said upper right angle section having a substantially square internal cavity for receiving said upper bar;

c) said second means comprises a clamp fixed to the lower end of said upper right angle section having a substantially square internal cavity for receiving said lower right angle section; and d) said upper right angle section and said lower right angle section being in mirror image relationship to one another whereby said frame is generally c-shaped.

3. Apparatus as defined in claim 2 further includes:

a) a first tightening screw associated with said first clamp; and b) a second tightening screw associated with said second clamp.

4. Apparatus as defined in claim 3 comprising:

a) said means for maintaining the axis of said first sleeve vertical comprises a vertical cylindrical clamp fixed to an end of said upper bar; and b) said means for selectively fixing the height of said first sleeve comprises a tightening screw associated with said vertical cylindrical clamp.

5. Apparatus as defined in claim 4 wherein:

a) said means for holding said second sleeve comprises a horizontal cylindrical clamp fixed to an end of said lower angle bar; and b) said means for selectively fixing the horizontal disposition of said second sleeve comprises a tightening screw associated with said horizontal cylindrical clamp.

6. Apparatus for internally positioning an elongated surgical tool with respect to a bone comprising, in combination:

a) an adjustable frame;

b) said frame including a first means for adjustably vertically positioning a first sleeve and a second means for adjustably horizontally positioning a second sleeve wherein said first sleeve and said second sleeve define a common plane;

c) said first sleeve being arranged to slidably receive a drill bit;

d) said second sleeve being arranged to receive an anchor pin in slidable relationship;

e) a vertical clamp for fixing the position of said first sleeve with respect to said bone;

f) a horizontal clamp for fixing the position of said second sleeve with respect to said bone;

g) a horizontal bar fixed to said vertical clamp for adjustably fixing the position of said vertical clamp with respect to said frame;

h) a first frame clamp fixed to a first end of an upper right angle section for receiving said horizontal bar;

i) means for adjustably fixing the position of said second sleeve with respect to said frame; and j) a second frame clamp fixed to a first end of a lower right angle section for receiving said horizontal clamp.

7. Apparatus as defined in claim 6 further including a third frame clamp fixed to the second end of said upper right angle section for receiving the second end of said lower right angle section so that said upper and lower right angle sections are positioned in mirror image relation to one another.

* * * * *